(12) United States Patent
Jin et al.

(10) Patent No.: US 10,995,123 B2
(45) Date of Patent: May 4, 2021

(54) PYRUVATE TRANSPORTER

(71) Applicant: IUCF-HYU (INDUSTRY-UNIVERSITY COOPERATION FOUNDATION HANYANG UNIVERSITY), Seoul (KR)

(72) Inventors: EonSeon Jin, Seoul (KR); Kwang Suk Chang, Seoul (KR); Seung Beom Seo, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 0 days.

(21) Appl. No.: 16/608,022

(22) PCT Filed: Apr. 18, 2018

(86) PCT No.: PCT/KR2018/004510
§ 371 (c)(1),
(2) Date: Oct. 24, 2019

(87) PCT Pub. No.: WO2018/199546
PCT Pub. Date: Nov. 1, 2018

(65) Prior Publication Data
US 2020/0190150 A1    Jun. 18, 2020

(30) Foreign Application Priority Data

Apr. 25, 2017  (KR) .......................... 10-2017-0052876

(51) Int. Cl.
C12N 15/79    (2006.01)
C12P 7/64     (2006.01)
(Continued)

(52) U.S. Cl.
CPC .............. *C07K 14/405* (2013.01); *C12N 1/12* (2013.01); *C12N 1/16* (2013.01); *C12N 1/20* (2013.01); *C12N 15/79* (2013.01); *C12P 7/649* (2013.01)

(58) Field of Classification Search
None
See application file for complete search history.

(56) References Cited

U.S. PATENT DOCUMENTS

2016/0237441 A1* 8/2016 Nielsen ................ C12N 9/0051

FOREIGN PATENT DOCUMENTS

KR    10-2013-0128241 A    11/2013

OTHER PUBLICATIONS

Geneseq Accession No. AWF62314, published Apr. 2, 2009 (Year: 2009).*

(Continued)

*Primary Examiner* — Richard C Ekstrom
(74) *Attorney, Agent, or Firm* — Sughrue Mion, PLLC

(57) ABSTRACT

The present invention relates to a novel pyruvate transporter. By using the novel enzyme of the present invention, biomass and metabolite production amounts of a microorganism can be increased. Accordingly, by massively incubating the microorganism having improved growth characteristics, biomass or target protein production efficiency, or biodiesel production efficiency can be improved, and bioenergy production costs can be reduced, which may bring out the effect of industrial development.

9 Claims, 6 Drawing Sheets

Specification includes a Sequence Listing.

```
Sbjct: Phaeodactylum tricornutum predicted protein [Phaeodactylum tricornutum CCAP 1055/1]
Sequence ID: ref|XP_002179421.1| Predicted Na+-dependent transporter Identities         Positives        Gaps
154/314(49%)       205/314(65%)     1/314(0%)
BASS2  94  YEKIIELLTTLFPLWVILGTLVGIFFPSLVTWLETDLFTLGLGFLMLSMGLTLTFEDFRR  153
           YEK  + TTLFPLW +L T +  +   PS   W  T+ FT GL  LMLSMG+TLT  DF++
PtPTP  1   YEKTANVATTLFPLWTVLFTGLALKSPSSFAWFTTRYFTAGLAALMLSMGITLTFNDFKK  60

BASS2  154 CLPNPWTVGVGFLAQYMIKFILGFLIAMTLKLSAPLATGLILVSCCPGGQASWVATYISK  213
           P   + F  Y + P+L  +    L   L G++LV  GGQASK+ TYI++
PtPTP  61  VAARPNATLMQFALCYGMMPMLALGLGKAFALEPALIAGMVLVGSINGGQASNLCTYIAR  120

BASS2  214 GNVALSVLMTTCSTIGAITMTPLLTKLLAGQLVPVDAAGLALSTFQVVEVPTIIGVLANE  273
           GNVALSV+MTT +T+GAI+MTPLL K L G +VPVDAAG+A ST QVVL P +IG+  N+
PtPTP  121 GNVALSVLMTTATTLGAIVMTPLLCKSLLGAVVPVDAAGIAKSTIQVVLAPTVIGMTTNK  180

BASS2  274 FFPKFTSKIITVTPLIGVILTTLLCASPIGQVADVLKTQGAQLILPVALLHAAAFAIGYW  333
           FFP+F  RI+   F++GV+ T LL AS + QVA+ +   G +L +P+ L+H     +GY
PtPTP  181 FFPRFVEKTLPFRPVVGVVSTCLLVASAVAQVABPILNAGLRLQIPIMLIHLLGGLVGYI  240

BASS2  334 ISKFS-FGECTSRTISIECGMQSSALGFLLAQKHFTNPLVAVPSAVSVVCMALGGSGLAV  392
           + + + FGE+++RT++IE  M+SSA GFLLA+ HF +   VPSAVSVV MAL GS IAV
PtPTP  241 LPRLYGFGETSAPTMAIETSMKSSAFGFLLAKLHFGDIAARVFSAVSVVWMALIGSLLAV  300

BASS2  393 FWRNLFIPADDKED  406
           WR +P+    K D
PtPTP  301 VWRYIPVETTGKFD  314
```

(51) Int. Cl.
*C07K 14/405* (2006.01)
*C12N 1/12* (2006.01)
*C12N 1/16* (2006.01)
*C12N 1/20* (2006.01)

(56) References Cited

OTHER PUBLICATIONS

Geneseq Accession No. AWF62317, published Apr. 2, 2009 (Year: 2009).*
GenBank: OEU19722.1: Bass Family Transporter. Sodium Ion/bile Acid [Fragilariopsis cylindrus CCMP1102], Sep. 30, 2016), 2 pages.
Seungbeom Seo, et al., "Positive effects on biomass production of Phaeodactylum tricornutum overexpressing phosphoenolpyruvale carboxylase", The Korean Society for Biotechnology and Bioengineering Conference, Oct. 2016. p. 409, PO507.
Tsuyoshi Furumoto, et al., "A plastidial sodium-dependent pyruvate transporter", Nature, Aug. 25, 2011, pp. 472-475, vol. 476.
Matilde Skogen Chauton, et al., "Gene Regulation of Carbon Fixation, Storage, and Utilization in the Diatom *Phaeodactylum tricornutum* Acclimated to Light/Dark Cycles", Plant Physiology, Feb. 2013, pp. 1034-1048, vol. 161.
International Search Report for PCT/KR2018/004510 dated Jul. 26, 2018 [PCT/ISA/210].

* cited by examiner

Fig. 1

```
Sbjct: Phaeodactylum tricornutum predicted protein [Phaeodactylum tricornutum CCAP 1055/1]
Sequence ID: ref|XP_002179421.1| Predicted Na⁺-dependent transporter Identities          Positives          Gaps
154/314(49%)       205/314(65%)       1/314(0%)
BASS2  94   YEKIIELLTTLFPLWVILGTLVGIFKPSLVTWLETDLFTLGLGFLMLSMGLTLTFEDFRR  153
            YEK  + TTLFPLW +L T + +  PS   W  T+ FT GL  LMLSMG+TLT  DF++
PtPTP   1   YEKTANVATTLFPLWTVLFTGLALKSPSSFAWFTTEYFTAGLAALMLSMGITLTPNDFKK  60

BASS2  154  CLRNPWTVGVGFLAQYMIKPILGFLIAMTLKLSAPLATGLILVSCCPGGQASNVATYISK  213
                  P  + F  Y + P+L  +     L  L G++LV    GGQASN+ TYI++
PtPTP   61  VAARPNATLMQFALCYGMMPMLALGLGKAFALEPALIAGMVLVGSINGGQASNLCTYIAR  120

BASS2  214  GNVALSVLMTTCSTIGAIIMTPLLTKLLAGQLVPVDAAGLALSTFQVVLVPTIIGVLANE  273
            GNVALSVLMTT +T+GAI+MTPLL K L G +VPVDAAG+A ST QVVL P +IG+  N+
PtPTP  121  GNVALSVLMTTATTLGAIVMTPLLCKSLLGAVVPVDAAGIAKSTIQVVLAPIVIGMTTNK  180

BASS2  274  FFPKFTSKIITVTPLIGVILTTLLCASPIGQVADVLKTQGAQLILPVALLHAAAFAIGYW  333
            FFP+F  KI+    P++GV+ T LL AS +  QVA+ +    G +L +P+ L+H    +GY
PtPTP  181  FFPRFVEKILPFAPVVGVVSTCLLVASAVAQVAEPILNAGLRLQIPIMLIHLLGGLVGYI  240

BASS2  334  ISKFS-FGESTSRTISIECGMQSSALGFLLAQKHFTNPLVAVPSAVSVVCMALGGSGLAV  392
             + + + FGE+++RT++IE M+SSA GFLLA+ HF +    VPSAVSVV MAL GS LAV
PtPTP  241  LPRLTGFGETSARTMAIETSMKSSAFGFLLAKLHFGDYAARVPSAVSVVWMALIGSLLAV  300

BASS2  393  FWRNLPIPADDKDD    406
            WR +P+    K D
PtPTP  301  VWRYIPVETTGKFD    314
```

Fig. 2

```
       414964 CGGCAACGGTAGGTACCAATCGACAACGATACGGCACACATCGATACAATACCAACCGAGCGCGAGAGAG 414895
       414894 GATTCCGGTTTCACCACAAAGCAGCGATCCTCACGGTCTTTCTTCCTATATCCTCTTCTTGGTACAGTCT 414825
       414824 CTCCAAGCCGCTAACGGTGACGCACCCGGAAAATCCTTCGGTCAGAAACTCTTTGAAGGCTACGAAAAGA 414755
  eg -2        L  Q  A  A  N  G  E  A  A  G  K  S  F  G  Q  K  L  F  E  G  Y  E  K
       414754 CGGCCAACGTGGCCACGACGCTCTTTCCCCTCTGGACCGTCCTTTTCACCGGTCTCGCCCTCAAAAGCCC 414685
  eg -2        T  A  N  V  A  T  T  L  F  P  L  V  T  V  L  F  T  G  L  A  L  K  S  P
       414684 GTCCTCTTTCGCCTGGTTTACCACCGAATACTTTACGGCGGGTCTGGCCGCACTCATGCTCTCCATGGGC 414615
  eg -2        S  S  F  A  W  F  T  T  E  Y  F  T  A  G  L  A  A  L  M  L  S  M  G
       414614 ATCACGCTCACCCCCAACGATTTCAAAAAGGTAGCCGCCCGTCCCAACGCCACGCTCATGCAGTTTGCTC 414545
  eg -2        I  T  L  T  P  N  D  F  K  K  V  A  A  R  P  N  A  T  L  M  Q  F  A
       414544 TCTGTTACGGAATGATGCCAATGCTGGCTCTGGGACTCGGTAAGGCTTTCGCCTTGGAACCCGCCTTGAT 414475
  eg -2        L  C  Y  G  M  M  P  M  L  A  L  G  L  G  K  A  F  A  L  E  P  A  L  I
       414474 TGCCGGTATGGTGTTGGTCGGGTCCATCAACGGTGGACAAGCTTCCAACTTGTGTACCTACATTGCCCGG 414405
  eg -2        A  G  M  V  L  V  G  S  I  N  G  G  Q  A  S  N  L  C  T  Y  I  A  R
       414404 GGTAACGTCGCCTTGTCGGTCCTCATGACCACCGCTACCACCTTGGGCGCCATCGTCATGACCCCGCTCT 414335
  eg -2        G  N  V  A  L  S  V  L  M  T  T  A  T  T  L  G  A  I  V  M  T  P  L
       414334 TGTGCAAGAGCCTCCTGGGGGCCGTCGTACCCGTCGACGCCGCTGGGATCGCCAAATCCACCATTCAGGT 414265
  eg -2        L  C  K  S  L  L  G  A  V  V  P  V  D  A  A  G  I  A  K  S  T  I  Q  V
       414264 ACGTTCATCGCTGTCCGCCTAGTAACGCGTAGTTGCAGTACACCACCCACTCGTTGCACCGTTCGTCGAT 414195
  eg -2        R  S  S  L  S  A  *  *  R  V  V  A  V  H  H  P  L  V  A  P  F  V  D
       414194 GGAGGTTCCTGGAGAGCAGAGCTCACACATTAGTGTTGTTGTCGCTACGTTTGCAGGTCGTGCTAGCTCC 414125
  eg -1        V  R  F  L  E  S  R  A  H  T  L  V  L  L  S  L  R  L  Q  V  V  L  A  P
       414124 GATTGTGATTGGTATGACCACCAACAAATTCTTCCCCCGGTTTGTCGAGAAAATCCTTCCGTTCGCCCCC 414055
  eg -1        I  V  I  G  M  T  T  N  K  F  F  P  R  F  V  E  K  I  L  P  F  A  P
       414054 GTTGTTGGGGTCGTCTCGACCTGTTTACTGGTTGCCAGTGCGGTCGCTCAAGTTGCCGAACCCATCCTGA 413985
  eg -1        V  V  G  V  V  S  T  C  L  L  V  A  S  A  V  A  Q  V  A  E  P  I  L
       413984 ACGCCGGATTGCGTTTACAGATCCCCATAATGTTGATTCATCTCTTTTGGGAGGACTCGTCGGCTACATTTT 413915
  eg -1        N  A  G  L  R  L  Q  I  P  I  M  L  I  H  L  L  G  G  L  V  G  Y  I  L
       413914 GCCCCGTTTGACCGGATTTGGCGAGACGTCCGCCCGCACCATGGCGATTGAAACCTCCATGAAGAGCTCC 413845
  eg -1        P  R  L  T  G  F  G  E  T  S  A  R  T  M  A  I  E  T  S  M  K  S  S
       413844 GCCTTTGGTTTTCCTCTTGGCCAAGCTGCACTTTGGTGACTACGCGGCCCGTGTGCCTTCGCCGTCTCCG 413775
  eg -1        A  F  G  F  L  L  A  K  L  H  F  G  D  Y  A  A  R  V  P  S  A  V  S
       413774 TCGTGTGGATGGCCTTGATCGGTTCCTTGTTGGCCGTCGTATGGCGGTACATCCCGGTGGAAACCACCGG 413705
  eg -1        V  V  W  M  A  L  I  G  S  L  L  A  V  V  W  R  Y  I  P  V  E  T  T  G
       413704 CAAGTTCGACCGTTCCTTGGTCGACAAGTACCCGCCCTTTAGTCCCAAGCGAGCGTTTGGAAAATTCCTA 413635
  eg -1        K  F  D  R  S  L  V  D  K  Y  P  P  F  S  P  K  R  A  F  G  K  F  L
       413634 CAGTCGGTTGGTCTCCAAAAGAAGGATGACGACGACACCGACACCCTCGGTGACGAAGCGTAGTTTC 413565
       413564 TCGATGACGGGATATTGGACCGTCGTGTCGTTCACCAAAGACGCGCACAAACGTATACGTAAACAAAACT 413495
```

PYRUVATE TRANSPORTER

CROSS REFERENCE TO RELATED APPLICATIONS

This application is a National Stage of International Application No. PCT/KR2018/004510, filed on Apr. 18, 2018, which claims priority from Korean Patent Application No. 10-2017-0052876, filed on Apr. 25, 2017.

TECHNICAL FIELD

The present invention relates to a novel pyruvate transporter and use thereof.

BACKGROUND ART

Microalgae, which are the subjects of basic research because they have intracellular reaction mechanisms such as photosynthesis, have recently attracted attention as a next generation feedstock for advanced biofuels such as biodiesel and other hydrocarbons (Kilian et al., 2011). Compared to ground crops, microalgae are advantageous in that they do not require arable land, and many species thereof can be cultured in aquatic environments containing sewage or salt.

However, there are limitations in economically producing biofuels from unmodified wild-type microalgae. A powerful molecular biological tool is needed as one of species optimization tools for overcoming such limitations, and thus, research thereinto is underway (Radakovits et al., 2010). For a long time, most molecular biological genetic studies have been carried out on the green alga *Chlamydomonas reinhardtii*. Thereby, molecular biological methods such as transgene expression and gene knockdown have been mostly developed with regard to *C. reinhardtii* species.

Recently, research tools for diatoms, which are attracting attention for industrial applications, or other microalgae are being rapidly developed (Radakovits et al. 2010). Using nutrient limitation, heterotrophic growth conditions, genetic engineering, and the like among various tools, research into increase of a useful lipid content according to biomass increase in microalgae is actively underway. To date, positive research results for the development of biofuels through genetic modification using useful genes to change a biomass or lipid content in microalgae have been continuously obtained (Kilian et al., 2011; Kranz et al., 2013).

Accordingly, there is still a need for development of novel proteins, vectors, or transformants for genetic engineering modification which are capable of increasing biomass production amounts or lipid contents in external open ponds or unopened photobioreactors of commercially important microalgae, i.e., imposing an ideal growth characteristic, among various considerations related to the growth and culture of microalgae.

DISCLOSURE

Technical Problem

Therefore, the present invention has been made in view of the above problems, and it is one object of the present invention to provide a novel pyruvate transporter. In particular, a *Phaeodactylum tricornutum*-derived pyruvate transporter capable of controlling transport of pyruvate known as a very important precursor of metabolites, such as fatty acids, terpenoids, and amino acids, present in the plastid and involved in biosynthesis, and thus, affecting a biomass or metabolite production amount increase in microalgae; and a gene encoding the pyruvate transporter were newly identified. Accordingly, it is another object of the present invention to provide a vector including the gene, a transformant including the vector, and a method of producing biomass or biodiesel using the transformant.

Technical Solution

To accomplish the above objects, the present inventors have continued research to increase biomass of a microorganism or the synthesis of metabolites in a biosynthesis process using a microorganism. As a result, a novel pyruvate transporter that plays an important role in a metabolic process of a microorganism was newly identified. In particular, it was confirmed through specific experiments that lipid content and biomass production amount in microalgae can be increased by using the newly identified pyruvate transporter. A nucleic acid molecule encoding the pyruvate transporter was inserted into an overexpression vector to construct a transformant. It was confirmed that biomass and lipid contents in the transformed microalgae increased, thus completing the present invention.

In such an aspect, the present invention provides a pyruvate transporter including an amino acid sequence of SEQ ID NO: 1.

In addition, the present invention provides a nucleic acid molecule encoding the pyruvate transporter.

In addition, the present invention provides a vector including the nucleic acid molecule.

In addition, the present invention provides a transformant including the vector.

In addition, the present invention provides a method of producing biomass or biodiesel, the method including incubating the transformant.

In addition, the present invention provides a composition for producing biomass, including one or more selected from the group consisting of a pyruvate transporter including an amino acid sequence of SEQ ID NO: 1 and a nucleic acid molecule encoding the pyruvate transporter.

In addition, the present invention provides a method of transforming a microorganism, the method including introducing a nucleic acid molecule includes a sequence of SEQ ID NO: 1 and encoding a pyruvate transporter; and a promoter for overexpressing the nucleic acid molecule into a microorganism.

Advantageous Effects

As apparent from the fore-going description, by using a novel enzyme of the present invention, biomass and metabolite production amounts of a microorganism can be increased. Accordingly, by mass-incubating the microorganism having improved metabolic characteristics, the productivity of a target substance and the production efficiency of biodiesel can be improved, and bioenergy production costs can be reduced, which may facilitate effect of industrial development.

DESCRIPTION OF DRAWINGS

FIG. 1 illustrates a gene analysis result for ortholog search using BASS2 protein of a plant according to an embodiment of the present invention.

FIG. 2 illustrates an analysis result, made at the JGI site, of a sequence of a protein predicted to be a *Phaeodactylum* tricornutum-derived pyruvate transporter according to an embodiment of the present invention.

Figure 3:
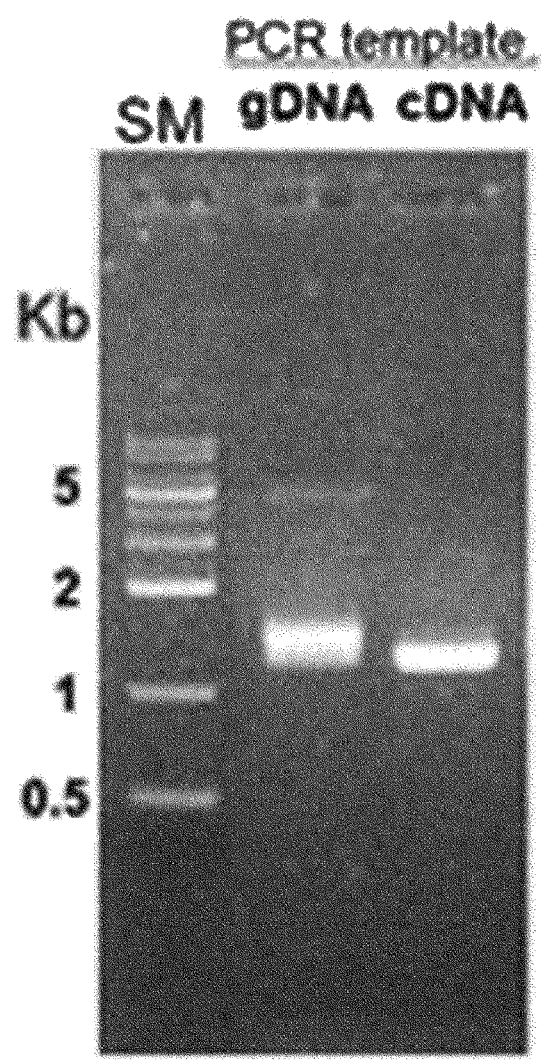

FIG. 3 illustrates a result of PCR performed to confirm whether RNA is generated from a gene expected based on JGI genome analysis according to an embodiment of the present invention.

Figure 4A:
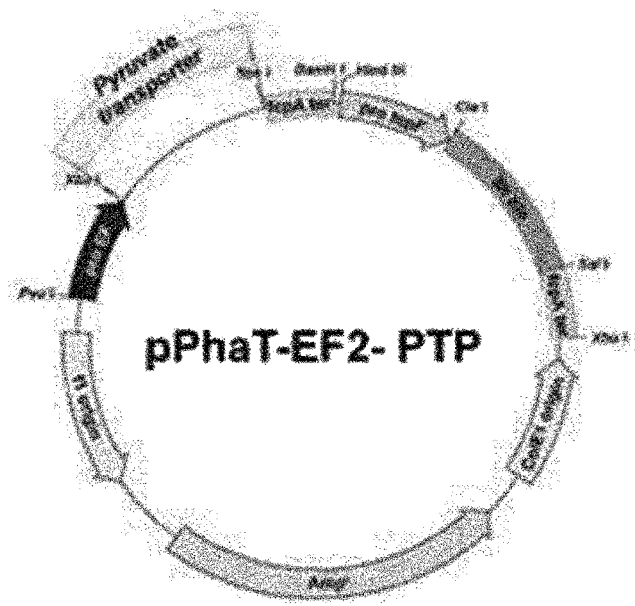

FIG. 4a illustrates a schematic diagram of a recombinant overexpression vector of a pyruvate transporter manufactured according to an embodiment of the present invention.

Figure 4B:
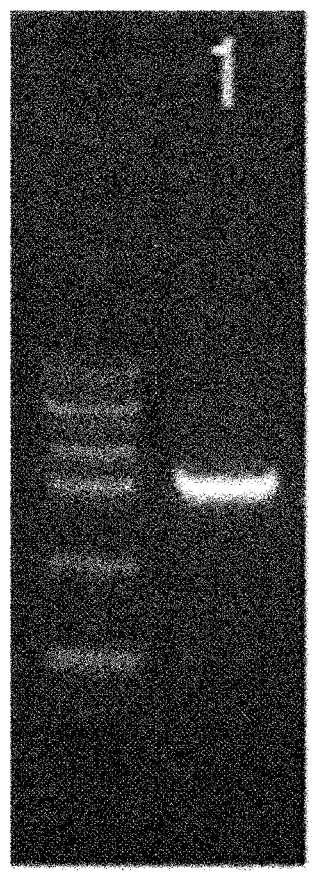

FIG. 4b illustrates a PCR result of a plasmid structure according to an embodiment of the present invention.

Figure 5:
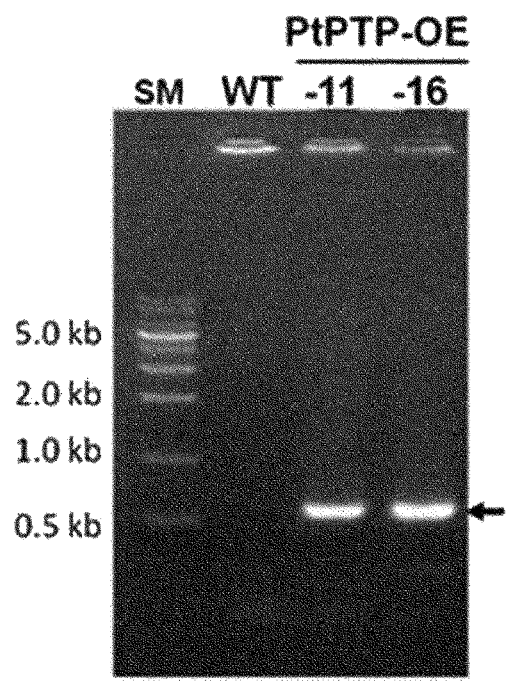

FIG. 5 illustrates a PCR result to confirm whether a foreign gene is inserted into transformants manufactured according to an embodiment of the present invention.

Figure 6:
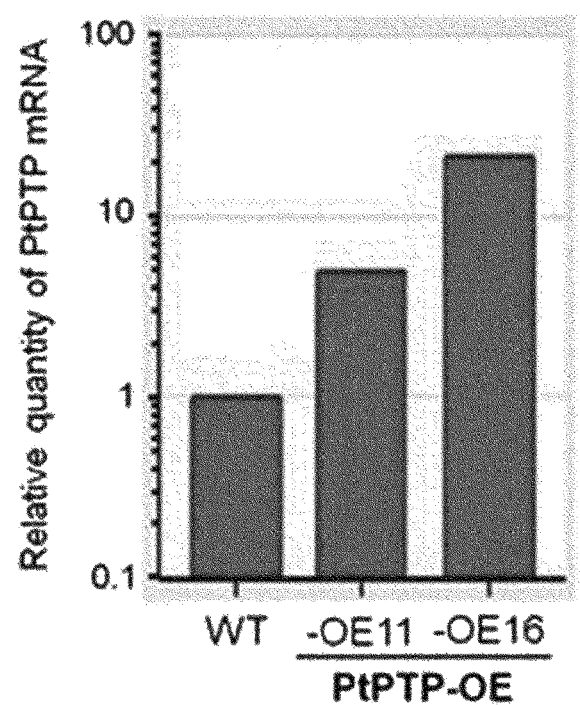

FIG. 6 illustrates mRNA expression levels of an inserted gene (PtPTP) in transformants manufactured according to an embodiment of the present invention.

Figure 7:
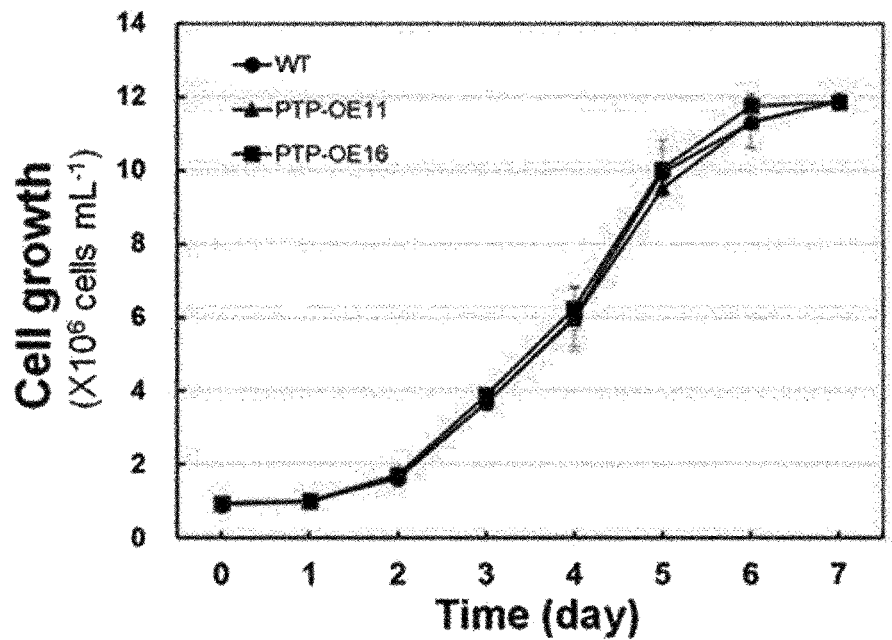

FIG. 7 illustrates growth curves of transformants manufactured according to an embodiment of the present invention.

Figure 8:
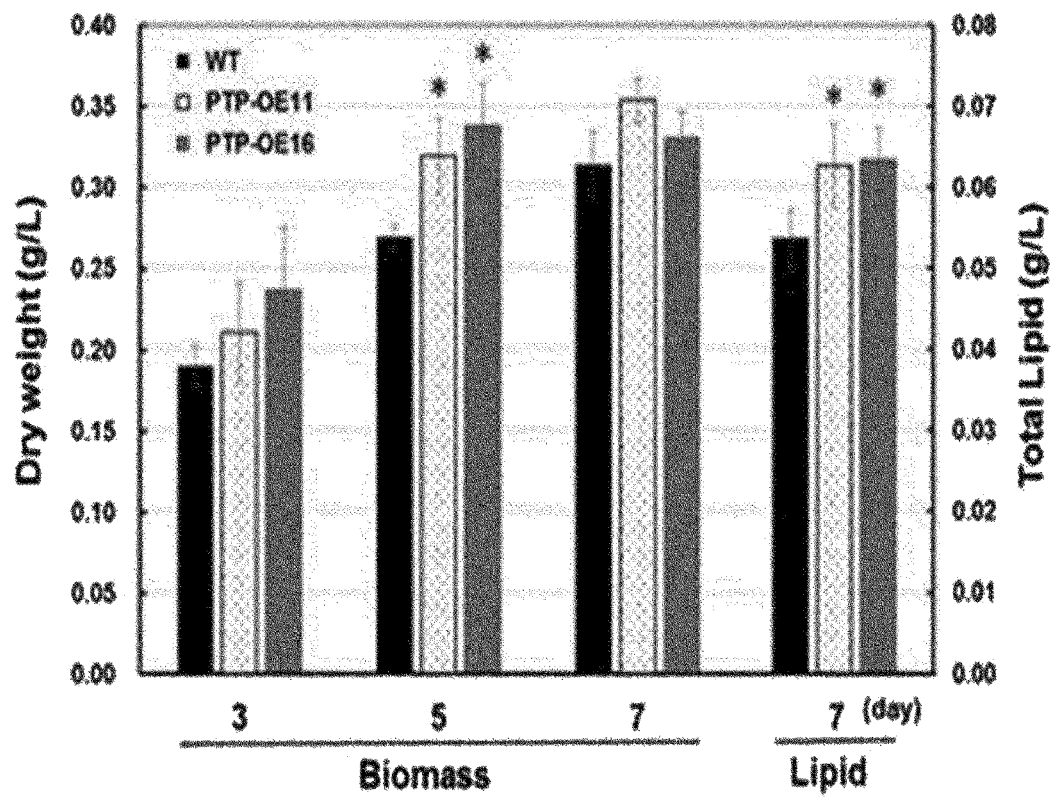

FIG. 8 illustrates biomass and lipid contents in transformants manufactured according to an embodiment of the present invention.

MODES OF THE INVENTION

As the invention allows for various changes and numerous embodiments, particular embodiments will be described in detail in the written description. However, this is not intended to limit the present invention to particular modes of practice, and it is to be appreciated that all changes, equivalents, and substitutes that do not depart from the spirit and technical scope of the present invention are encompassed in the present invention.

Hereinafter, the present invention is described in more detail.

The present invention provides a microalgae-derived novel pyruvate transporter.

In the present invention, "pyruvate transporter (pyruvate transporter protein)" refers to a protein involved in delivery of pyruvate to the plastid. A large number of proteins serving to transport pyruvate is known to be present in C4 plants, but it has not been known whether pyruvate transporters are present in diatoms such as Phaeodactylum tricornutum. The present inventors have tried to find a diatom-derived transporter and, as a result, identified an amino acid sequence of a pyruvate transporter and a sequence of a nucleic acid molecule encoding the amino acid sequence, through genome analysis of Phaeodactylum tricornutum, and named the protein "pyruvate transporter plastid-type protein (PtPTP)." In addition, it was confirmed through experimentation that, when the transporter is inserted into and overexpressed in a microorganism such as microalgae, biomass and lipid contents in the transformed microorganism are increased by about 20% or more, compared to a wild type.

Accordingly, a pyruvate transporter of the present invention may be a Phaeodactylum Tricornutum-derived pyruvate transporter. In the present specification, "pyruvate transporter" may be used interchangeably with terms such as pyruvate transporter plastid-type protein (PtPTP).

The pyruvate transporter of the present invention may include an amino acid sequence of SEQ ID NO: 1. In addition, the pyruvate transporter of the present invention includes functional equivalents. The "functional equivalents" have a sequence homology of at least 70%, preferably 80% or more, more preferably 90% or more, even more preferably 95% or more, with an amino acid sequence represented by SEQ ID NO: 1 as results of addition, substitution, or deletion of an amino acid. The "functional equivalents" refer to proteins having physiological activity substantially identical to that of the protein represented by SEQ ID NO: 1. "Substantially identical physiological activity" means activity of transporting pyruvate in a microorganism.

Preferably, the novel pyruvate transporter of the present invention may have the amino acid sequence of SEQ ID NO: 1.

The pyruvate transporter referred to in the present invention includes recombinant proteins produced using nucleic acid molecules encoding the pyruvate transporter as well as proteins isolated and purified from Phaeodactylum tricornutum.

In such an aspect, the present invention provides nucleic acid molecules encoding a pyruvate transporter.

In the present invention, the "nucleic acid molecules" encompass DNA (gDNA and cDNA) and RNA molecules. A nucleotide which is a basic constituent unit of a nucleic acid molecule may be a native nucleotide or an analogue thereof with a modified sugar or base site.

According to an embodiment of the present invention, a nucleic acid molecule of the present invention may include a nucleotide sequence of SEQ ID NO: 2 or a nucleotide sequence of SEQ ID NO: 3. The nucleotide sequence of SEQ ID NO: 2 is cDNA obtained from the pyruvate transporter of the present invention, and the nucleotide sequence of SEQ ID NO: 3 is gDNA obtained through genome analysis of Phaeodactylum tricornutum.

The protein or the nucleic acid molecule of the present invention may have a mutation in a range within the activity or functions of the pyruvate transporter are not affected. In addition, it is apparent to those skilled in the art that the pyruvate transporter of the present invention or a nucleic acid molecule encoding the same is not limited to an amino acid sequence or nucleotide sequence described in the attached sequence list. In particular, a mutation in a nucleotide may not result in a change in a protein. Such a nucleic acid may include a nucleic acid molecule including functionally equivalent codons or codons (for example, due to degeneracy of codons, there are six codons for arginine or serine) encoding the same amino acid, or codons encoding a biologically equivalent amino acid. In addition, the present invention may even include a nucleotide mutation that can change the protein itself of the pyruvate transporter so long as a protein having almost the same function or activity as the function or activity of the pyruvate transport of the present invention is obtained.

Accordingly, nucleotide sequences substantially identical to a nucleotide sequence of the nucleic acid molecule encoding the pyruvate transporter of the present invention are interpreted as being included in the scope of the present invention. "Substantially identical" sequences refer to sequences showing at least 80% homology, more preferably 90% homology, most preferably 98% homology when a certain sequence is aligned to the sequence of the present invention to maximally correspond thereto and the aligned sequence is analyzed using an algorithm commonly used in the art. Such a sequence comparison may be performed using an alignment method and algorithm for sequence comparison commonly known in the present invention.

The nucleic acid molecule may be a gene construct including a nucleic acid molecule encoding a pyruvate transporter. In the present invention, the term "expression construct" is defined as a nucleic acid molecule including only a minimum element for protein expression in a cell. The expression construct of the present invention additionally includes restriction enzyme recognition sequences for cloning a foreign protein-encoding nucleotide sequence operably linked to a promoter sequence thereof. Restriction enzymes for restriction enzyme recognition sequences included in the expression construct of the present invention are not specifically limited and may include, for example, EcoRI, EcoRII, BamHI, HindIII, TaqI, NotI, HinfI, Sau3A, PovII, SmaI, HaeIII, HgaI, AluI, EcoRV, EcoP15I, KpnI, PstI, SacI, SalI, ScaI, SpeI, SphI, StuI, XbaI, and the like without being limited thereto. In the present invention, "operably linked" refers to a functional linkage between a nucleic acid expression control sequence (e.g., promoter sequence) and another nucleic acid sequence. By the functional linkage, the control sequence can control transcription and/or translation of another nucleic acid sequence. In the present invention, examples of a foreign protein include any proteins that can be expressed for beneficial transformation of algae without being specifically limited. A polyadenylation sequence, as a transcription termination sequence, may be included in the expression construct of the present invention.

The present invention also provides a vector that includes a nucleic acid molecule encoding a pyruvate transporter.

A vector system of the present invention may be constructed by various methods known in the art. Particular examples of the methods are described in Sambrook et al., Molecular Cloning, A Laboratory Manual, Cold Spring Harbor Laboratory Press (2001), which is incorporated herein by reference.

In the present invention, the "vector," which refers to a recombinant DNA molecule including a desired coding sequence and an appropriate nucleic acid sequence that is essential for expressing an operably linked coding sequence in a particular host organism, may be used interchangeably with "transformation vector", "expression vector", or the like. The appropriate nucleic acid sequence may be a promoter and may additionally include an enhancer, a transcription terminator, a polyadenylation signal, and the like.

Since the pyruvate transporter of the present invention is derived from eukaryotic cells, in consideration of culture convenience, eukaryotic cells may be used as a host. Promoters, enhancers, transcription terminators and polyadenylation signals available in eukaryotic cells are known in the art. The vector may be an expression vector into which the base sequence of the gene is inserted and thus which may be directly introduced into eukaryotic cells.

Meanwhile, the vector of the present invention includes an antibiotic resistance gene commonly used in the art, as a selection marker. For example, there are genes resistant to zeocin, ampicillin, gentamicin, carbenicillin, chloramphenicol, streptomycin, kanamycin, geneticin, neomycin, phleomycin, and tetracycline. In addition, the expression vector of the present invention may additionally include a gene encoding a reporter molecule (e.g., luciferase or beta-glucuronidase).

The vector may aim to overexpress a pyruvate transporter or a nucleic acid molecule encoding the same in a transformant. When the pyruvate transporter of the present invention is overexpressed in a microorganism, production of metabolites may increase. For example, when a pyruvate transporter is overexpressed in microalgae, transport of the pyruvate to the plastid increases so that the biomass of microalgae and a lipid content in the microalgae may increase. Accordingly, production efficiency in microalgae culture for the production of biodiesel and the like may be greatly improved. In addition, the pyruvate transporter of the present invention may be inserted into microorganisms such as yeast and bacteria to increase metabolites, thereby increasing the production of a target material.

"Overexpression" means to induce the expression of a target protein or gene to a higher level than in a wild-type microorganism. Overexpression may be performed using various known methods without being specifically limited.

For example, a ribosome-binding site or a promoter and a regulatory region located upstream of a structural gene may be mutated or introduced to increase a copy number of an appropriate gene, and an expression cassette into which the upstream of the structural gene is introduced may act in the same manner as in the structural gene. In addition, a nucleic acid molecule-inducible promoter that encodes the pyruvate transporter of the present invention may increase the expression of the nucleic acid molecule, or the expression of the nucleic acid molecule may be increased by a method of extending the lifespan of mRNA. Additionally, the nucleic acid molecule may be overexpressed by changing the composition of a medium and/or a culture technique.

A promoter for the overexpression may be any one known in the technical field of the present invention. For example, a fucoxanthin chlorophyll a/c binding protein (fcp) gene promoter used to develop a microalgae transformant, or Ef2 promoter (the content of KR10-1646991 is included as a reference) for non-photoperiodic expression of a foreign gene included in microalgae may be used, but the present invention is not limited thereto.

Accordingly, according to a particular embodiment, the vector of the present invention may further include a promoter for overexpressing a nucleic acid molecule encoding a pyruvate transporter. In particular, a transformation system capable of inducing overexpression of the pyruvate transporter was constructed using a transformation vector (pPhaT-EF2) developed to operate a promoter for non-photoperiodic expression of a foreign gene, and a transformant was produced using the transformation system. In addition, overexpression in the transformant was experimentally confirmed.

In such an aspect, the present invention provides a transformant including the vector that includes a nucleic acid molecule encoding a pyruvate transporter.

In the present invention, "transformation" refers to a molecular biological technique of allowing a DNA chain fragment of a foreign gene, which is different from native genes in a cell, or a plasmid including the foreign gene to penetrate into cells and to bind to native DNA in the cells, thereby altering genetic traits of the native DNA. In the present invention, transformation refers to a process of inserting a nucleic acid molecule encoding a pyruvate transporter together with a vector into a microorganism, preferably a microalgae. Accordingly, the transformant may be microalgae.

The vector may be transported into subject cells using methods, such as the $CaCl_2$ method (Cohen, S. N. et al., Proc. Natl. Acac. Sci. USA, 9:2110-2114 (1973)), Hannahan's method (Cohen, S. N. et al., Proc. Natl. Acac. Sci. USA, 9:2110-2114 (1973); and Hanahan, D., J. Mol. Biol., 166: 557-580 (1983)), the electroporation method (Dower, W. J. et al., Nucleic. Acids Res., 16:6127-6145 (1988)), and the particle transport method (Seo et al. 2015), known in the technical field of the present invention.

The vector injected into a microorganism may be expressed or induced to be overexpressed in the microorganism. In this case, transport of pyruvate actively occurs in the microorganism, resulting in active metabolite production.

In the present invention, a microorganism to be transformed may be cells, preferably prokaryotic cells or eukaryotic cells. Accordingly, the transformant may also be referred to as recombinant cells or a recombinant microorganism. The microorganism may be more preferably yeast, *E. coli*, or microalgae. When overexpression of a pyruvate transporter is induced in microalgae, transport of pyruvate to the plastid becomes active, thereby increasing a lipid content and a biomass production amount in the microalgae. In addition, when the pyruvate transporter of the present invention is introduced into a microorganism such as yeast, *E. coli* or microalgae, the metabolism of the microorganism becomes active, so that a production amount of a target substance may increase through the metabolism. The target substance refers to a substance to be produced by culturing a microorganism into which the pyruvate transporter of the present invention is introduced. For example, the target substance may be a protein, peptide, or the like produced by introducing a foreign gene, or a fatty acid obtained through a metabolic process of a microorganism. Accordingly, the transformant may be transformed yeast, *E. coli* or microalgae.

According to an embodiment of the present invention, the present inventors constructed a recombinant vector construct into which a gene encoding a pyruvate transporter; and a promoter for inducing overexpression of the pyruvate transporter were inserted, and injected the recombinant vector construct into *Phaeodactylum tricornutum*. As a result, two types of PTP gene overexpression transformants, *Phaeodactylum tricornutum* CCMP632 PtPTP-OE11 and *Phaeodactylum tricornutum* CCMP632 PtPTP-OE16, were identified through two-step selection, were deposited at the Korean Collection for Type Cultures (KCTC) on March 21, and were respectively given accession numbers of KCTC 18558P and KCTC 18559P. The transformants were again deposited at the International Depositary Authority on Apr. 24, 2017 and were respectively given accession numbers of KCTC13253BP and KCTC13254BP.

In addition, the present invention provides a biomass production method, the method including culturing a transformant including the vector including a nucleic acid molecule encoding a pyruvate transporter. The transformant may be a transformed microorganism, preferably transformed *E. coli*, yeast, or microalgae.

The transformant may be a transformant including an overexpression vector constructed to overexpress a nucleic acid molecule encoding a pyruvate transporter, or the culture may be carried out to induce overexpression of an introduced gene. Induction of overexpression has been described above.

When the transformant of the present invention is used, transport of a metabolite precursor, pyruvate, of a microorganism to the plastid becomes active, and thus, biosynthesis in a metabolic process of the microorganism actively occurs, thereby increasing the content of metabolites in the microorganism. For example, it was confirmed that, in microalgae recombined to overexpress the enzyme of the present invention, a biomass production amount and a lipid content increased. Accordingly, the microorganism recombined to overexpress the enzyme of the present invention may be utilized to increase the productivity of a target substance, biodiesel, etc.

The culture may be carried out under optimal culture conditions using a culture medium known in the technical field of the present invention in consideration of culture characteristics and the like of a transformant, and include culture performed in laboratories and industrial mass culture systems.

In addition, the present invention provides a method of transforming a microorganism, the method including introducing a nucleic acid molecule of SEQ ID NO: 1 encoding a pyruvate transporter protein; and a promoter overexpressing the nucleic acid molecule into a microorganism.

In addition, the present invention provides a composition for producing biomass including one or more selected from the group consisting of a pyruvate transporter and a nucleic acid molecule encoding the pyruvate transporter; a composition for increasing a biomass production amount; or a composition for increasing a metabolite content in a microorganism.

The transformation method includes introducing a foreign gene into a microorganism to increase biomass or a metabolite production amount in the microorganism. In such an aspect, the present invention provides a method of increasing a biomass production amount or metabolite content in a microorganism, the method including introducing a nucleic acid molecule encoding a pyruvate transporter protein; and a promoter for overexpressing the nucleic acid molecule into a microorganism.

The metabolite content increase or improvement may be, for example, increase or improvement of a lipid content in a microorganism.

The nucleic acid molecule and the promoter may be inserted into an expression vector.

In addition, such biomass or lipid in a microalgae may be utilized for production of biodiesel. When a microalgae having improved biomass production capacity and lipid content through overexpression of the pyruvate transporter of the present invention is used for production of biodiesel through scale-up, the production efficiency of biodiesel may be dramatically increased. In such an aspect, the present invention provides a method of producing biodiesel, the method including culturing the transformant of the present invention.

Conditions of the method of producing biodiesel may be varied depending upon the type, culture characteristics, and the like of a transformant transformed to include the pyruvate transporter. Commonly, diesel may be produced using a corresponding culture method of a transformant.

The transformant of the present invention has improved biomass and lipid production contents that can be converted into biodiesel, compared to a wild-type microorganism. Here, a culture product obtained from the transformant may be converted into biodiesel according to a method commonly used in the technical field of the present invention.

Now, the present invention will be described in more detail with reference to the following manufacturing examples and experimental examples. These examples are provided for illustrative purposes only and should not be construed as limiting the scope and spirit of the present invention.

EXAMPLE

[Example 1] Microalgae (*Phaeodactylum tricornutum*) Culture

*Phaeodactylum tricornutum* (*Phaeodactylum tricornutum* Bohlin, CCMP632) used in an experiment of the present invention was purchased from the National Center for Marine Algae and Microbiota (NCMA, USA). *Phaeodactylum tricornutum* was sterilely cultured on a f/2 medium at 20° C. The medium was made of artificial sea water, and 10 mM bicarbonate was added thereto. The cells were cultured on a shaking incubator at 130 rpm on a diurnal cycle of 12-hour light/12-hour dark in a 20° C. constant-temperature incubation room using a fluorescent lamp to provide a light quantity of 50 µmol·m$^{-2}$·s$^{-1}$.

[Example 2] Investigation of Pyruvate Transport-Related Gene and Acquirement of Full-Length Open Reading Frame (ORF) Gene 2-1. Investigation of Pyruvate Transport-Related Gene Pyruvate is known as a metabolic precursor of very important metabolites, such as fatty acids, terpenoids, and branched-chain amino acids, present in the plastid and involved in biosynthesis. To investigate the functions of a pyruvate transport which is important for the production of metabolites, gene analysis was carried out to find an ortholog present in the diatom *Phaeodactylum tricornutum* using a plant-derived pyruvate transporter (BASS2). First, an amino acid sequence of *Arabidopsis* BASS2 gene, At2g26900, was subjected to homology analysis at NCBI.

As an analysis result, it was confirmed that one gene located at *Phaeodactylum tricornutum* chromosome No. 6 showed a highest similarity of 49% with At2g26900, as shown in FIG. 1. The gene was defined as Pyruvate Transporter Plastid-type (PtPTP).

However, since the gene sequence (NCBI Reference Sequence: XM_002179385) shown in FIG. 1 was not a complete full-length gene, additional analysis was carried out to analyze and obtain a full-length gene sequence.

In particular, the pyruvate transport of *Phaeodactylum tricornutum* was analyzed at the JGI site (http://genome.jgi.doe.gov/Phatr2/Phatr2.home.html). As a result, it was confirmed that Protein ID 3046 was consistent with XM_002179385 at NCBI. However, it was confirmed that the gene was a partial sequence because it had no start codon and did not have an intact gene structure, as shown in FIG. 2. Accordingly, additional analysis was carried out to investigate a full-length sequence of the gene.

2-2. Acquirement of Pyruvate Transport Plastid-Type Full-Length Open Reading Frame (ORF)

To acquire a pyruvate transporter plastid-type full-length ORF, mRNA-based PCR was carried out.

To isolate RNA, wild-type *Phaeodactylum tricornutum* CCMP632 cells were harvested by centrifugation (2,000 g, 10 minutes) in an exponential growth phase, and RNA was isolated therefrom using an RNA purification kit, Hybrid-R (GeneAll Inc., Korea).

The isolated RNA was converted to cDNA using a high-capacity cDNA reverse transcription kit (Applied Biosystems Inc.).

To investigate the positions of a start codon and a stop codon of a pyruvate transport gene, positions were selected to include an entire full-length sequence based on the JGI genome sequence. Primers expected to correspond to the selected positions were prepared as follows:

```
Forward primer
                                           (SEQ ID NO: 4)
5'-ATGCCAATGATTGCTCCCACGATTTCTAC-3'

Reverse primer
                                           (SEQ ID NO: 5)
5'-ATATCCCCGTCATCGAGAAACTAC-3'
```

To investigate whether the selected ORF actually produced RNA, PCR was carried out using genomic DNA and RNA-derived cDNA, as templates, with the above primers. Here, Phusion High-Fidelity DNA Polymerase, manufactured by NEB, was used, and PCR conditions were follows: 35 cycles of initial denaturation (98° C., 30 sec) and denaturation (98° C., 10 sec), annealing (58° C., 20 sec), and elongation (72° C., 1 min), and final elongation (72° C., 10 min).

From the PCR result, it was confirmed that, in the PCR using the genomic DNA as a template, a relatively large band was generated, compared to the PCR using cDNA as a template, as shown in FIG. 3. The band size difference between the PCR products produced using genomic DNA and cDNA as templates is due to intron regions present in an ORF.

To clone the produced cDNA PCR product, the PCR product was gel-eluted, and the eluted PCR product was inserted into a cloning vector (Dr. Blunt TOPO cloning kit, Mgmed) for cloning. The obtained gene was subjected to sequence analysis, thereby confirming the following base sequence. The confirmed base sequence was analyzed, As a result, the base sequence was identified as a full-length ORF of a Pyruvate Transporter Plastid-type (PtPTP) gene.

```
SEQ ID NO: 1: Amino acid encoded by ORF of PtPTP
cDNA
MPMIAPTISTTTTSTALSATSLQAANGEAAGKSFGQKLFEGYEKTANVAT

TLFPLWTVLFTGLALKSPSSFAWFTTEYFTAGLAALMLSMGITLTPNDFK

KVAARPNATLMQFALCYGMMPMLALGLGKAFALEPALIAGMVLVGSINGG

QASNLCTYIARGNVALSVLMTTATTLGAIVMTPLLCKSLLGAVVPVDAAG

IAKSTIQVVLAPIVIGMTTNKFFPRFVEKILPFAPVVGVVSTCLLVASAV

AQVAEPILNAGLRLQIPIMLIHLLGGLVGYILPRLTGFGETSSRTMAIET

SMKSSAFGFLLAKLHFGDYAARVPSAVSVVWMALIGSLLAVVWRYIPVET

TGKFDRSLVDKYPPFSPKRAFGKFLQSVGLQKKDDDATPTPSVTEA

SEQ ID NO: 2: PtPTP cDNA full-length sequence
ATGCCAATGATTGCTCCCACGATTTCTACGACGACGACGTCCACTGCTCT

TTCCGCAACGTCTCTCCAAGCCGCTAACGGCGAGGCAGCCGGAAAATCCT

TCGGTCAGAAACTCTTTGAAGGCTACGAAAAGACGGCCAACGTCGCCACG

ACGCTCTTTCCCCTCTGGACCGTCCTTTTCACCGGTCTCGCCCTCAAAAG

CCCGTCCTCGTTCGCCTGGTTTACCACCGAATACTTTACGGCGGGTCTGG

CCGCACTCATGCTCTCCATGGGTATCACGCTCACCCCCAACGATTTCAAA

AAGGTAGCCGCCCGTCCCAACGCCACGCTCATGCAGTTTGCTCTCTGTTA

CGGAATGATGCCAATGCTGGCTCTGGGACTCGGTAAGGCTTTCGCCTTGG

AACCCGCCTTGATTGCCGGTATGGTGTTGGTCGGGTCCATCAACGGTGGA

CAAGCTTCCAACTTGTGTACCTACATTGCCCGGGGTAACGTCGCCTTGTC

GGTCCTCATGACCACCGCTACCACCTTGGGCGCCATCGTCATGACCCCGC

TCTTGTGCAAGAGCCTCCTGGGGGCCGTCGTACCCGTCGACGCTGCTGGG

ATCGCCAAGTCCACCATTCAGGTCGTGCTAGCTCCGATTGTGATTGGTAT

GACTACCAACAAATTCTTCCCCCGGTTTGTCGAGAAAATCCTTCCGTTCG

CCCCCGTTGTTGGGGTCGTCTCGACCTGTTTACTGGTTGCCAGTGCGGTC

GCTCAAGTTGCCGAACCCATCCTGAACGCCGGATTGCGTTTACAGATCCC
```

-continued

CATTATGTTGATTCATCTTTTGGGAGGACTCGTCGGCTACATTTTGCCTC

GTTTGACCGGATTTGGCGAGACGTCCTCCCGCACCATGGCGATTGAAACC

TCCATGAAGAGCTCCGCTTTTGGTTTCCTCTTGGCCAAGCTGCACTTTG

CGACTACGCGGCCCGTGTGCCTTCGGCCGTCTCCGTCGTGTGGATGCCT

TGATCGGTTCCTTGTTGGCCGTCGTATGGCGGTACATCCCGGTGGAAACC

ACCGGCAAGTTCGACCGTTCCTTGGTGGACAAGTACCCGCCCTTTAGTCC

CAAGCGAGCGTTTGGAAAATTCCTACAGTCGGTTGGTCTGCAAAAGAAGG

ATGACGACGCGACACCGACACCCTCGGTGACGGAAGCGTAGTTTCTCGAT

GACGGGGATAT

SEQ ID NO: 3: PtPTP sequence obtained from genomic DNA (ATG: start codon; TAG: stop codon; underlined: intron region; others: exon region)
ATGCCAATGATTGCTCCCACGATTTCTACGACGACGACGTCCACTGCTCT

TTCCGCAACGGTACGTACCAATCGACAACGATACCGCACACATCGATACA

ATACCAACCGAGCGCGAGAGAGGATTCCGGTTTCACCACAAAGCAGCGAT

CCTCACGGTCTTTCTTCCTATATCCTCTTCTTGGTACAGTCTCTCCAAGC

CGCTAACGGTGAGGCAGCCGGAAAATCCTTCGGTCAGAAACTCTTTGAAG

GCTACGAAAGACGGCCAACGTCGCCACGACGCTCTTTCCCCTCTGGACC

GTCCTTTTCACCGGTCTCGCCCTCAAAAGCCCGTCCTCTTTCGCCTGGTT

TACCACCGAATACTTTACGGCGGGTCTGGCCGCACTCATGCTCTCCATGG

GCATCACGCTCACCCCCAACGATTTCAAAAAGGTAGCCGCCCGTCCCAAC

GCCACGCTCATGCAGTTTGCTCTCTGTTACGGAATGATGCCAATGCTGGC

TCTGGGACTCGGTAAGGCTTTCGCCTTGGAACCCGCCTTGATTGCCGGTA

TGGTGTTGGTCGGGTCCATCAACGGTGGACAAGCTTCCAACTTGTGTACC

TACATTGCCCGGGGTAACGTCGCCTTGTCGGTCCTCATGACCACCGCTAC

CACCTTGGGCGCCATCGTCATGACCCCGCTCTTGTGCAAGAGCCTCCTGG

GGGCCGTCGTACCCGTCGACGCCGCTGGGATCGCCAAATCCACCATTCAG

GTACGTTCATCGCTGTCCGCCTAGTAACGCGTAGTTGCAGTACACCACCC

ACTCGTTGCACCGTTCGTCGATGGAGGTTCCTGGAGAGCAGAGCTCACAC

ATTAGTGTTGTTGTCGCTACGTTTGCAGGTCGTGCTAGCTCCGATTGTGA

TTGGTATGACCACCAACAAATTCTTCCCCCGGTTTGTCGAGAAAATCCTT

CCGTTCGCCCCCGTTGTTGGGGTCGTCTCGACCTGTTTACTGGTTGCCAG

TGCGGTCGCTCAAGTTGCCGAACCCATCCTGAACGCCGGATTGCGTTTAC

AGATCCCCATAATGTTGATTCATCTTTTGGGAGGACTCGTCGGCTACATT

TTGCCCCGTTTGACCGGATTTGGCGAGACGTCCGCCCGCACCATGGCGAT

TGAAACCTCCATGAAGAGCTCCGCCTTTGGTTTCCTCTTGGCCAAGCTGC

ACTTTGGTGACTACGCGGCCCGTGTGCCTTCGGCCGTCTCCGTCGTGTGG

ATGGCCTTGATCGGTTCCTTGTTGGCCGTCGTATGGCGGTACATCCCGGT

GGAAACCACCGGCAAGTTCGACCGTTCCTTGGTGGACAAGTACCCGCCCT

TTAGTCCCAAGCGAGCGTTTGGAAAATTCCTACAGTCGGTTGGTCTGCAA

AAGAAGGATGACGACGCGACACCGACACCCTCGGTGACGGAAGCGTAGTT

TCTCGATGACGGGGATAT

[Example 3] Construction of Expression Vector for Transformation

To insert the full-length ORF of the PtPTP gene cloned in Example 2 into a vector for transformation, the transformation system, pPhaT-EF2 vector construct (FIG. 4a), as constructed above was used. For easy insertion, primers (Forward primer 5'-TCTAGATGCCAATGATTGCTCC-CACGA-3' (SEQ ID NO: 6); Reverse primer 5'-TCTA-GACCCCGTCATCGAGAAACTAC-3'(SEQ ID NO: 7)) including an Xba I position linker were manufactured. The full-length cDNA of the PtPTP ORF gene was synthesized by the PCR method of Example 2. Obtained DNA fragments were cut with a restriction enzyme, Xba I, and then inserted into the pPhaT-EF2 expression vector that had been cut with restriction enzymes, Xba I and Spe I, thereby constructing a recombinant vector pPhaT-EF2-PTP (FIG. 4a). The pPhaT-EF2-PTP contained a zeocin-resistant gene, which allowed selection of zeocin-resistant transformants.

It was confirmed whether the constructed plasmid structure was successfully constructed, and a result thereof is shown in FIG. 4b.

[Example 4] Construction of Pyruvate Transporter Overexpression Transformant

Tungsten particles were coated with the constructed plasmid for transformation, and introduced into *Phaeodactylum tricornutum* by a biolistic bombardment (particle delivery) method. In particular, the plasmid DNA-coated tungsten particles were obtained by adding the plasmid, CaCl$_2$, and spermidine to tungsten particles M17 (Bio-rad, diameter: 1.1 µm) and mixing the same, followed by washing twice with 70% ethanol and 100% ethanol. The resultant product was placed and dried on a microcarrier, and then *Phaeodactylum tricornutum* plated on a medium was transformed by a particle bombardment method using a Biolistic Particle Delivery System PDS-1000/He (Bio-Rad Laboratories) fitted with 1550 psi rupture discs as recommended by a manufacturer. After transformation, the transformant was incubated under a light condition for 24 hours, and plated on a f/2 solid medium containing zeocin (100 ug/ml). After 3 weeks, zeocin-resistant transformant colonies were selected (Seo et al. 2015).

To investigate whether, in resistant colonies grown in the zeocin selection medium, a foreign gene inserted into genomic DNA thereof was stably present therein, genomic DNA PCR was performed. The colonies were transferred to a new solid medium and cultured for one week independently. Next, some microalgae were taken from the grown microalgae and released in distilled water (DW). Using genomic DNA from the diluted microalgae as a template, PCR was carried out with a forward primer (5'-CTGT-GAAGCCGTGGTGAATCTT-3'; SEQ ID NO: 8) at an EF2 promoter region and a reverse primer (5'-CCGGGCAATGTAGGTACACAAG-3'; SEQ ID NO: 9) at a PtPTP ORF region. For this PCR, rTaq 5XPCR Master Mix (ELPIS-Biotech, Daejeon, Korea) was used, and reaction conditions were as follows: denaturation temperature: 95° C., annealing temperature: 58° C., and elongation temperature: 72° C. (10 seconds each).

As shown in FIG. 5, it was conformed that the foreign gene was successfully inserted into transformants PtPTP-OE-11 and PtPTP-OE-16.

[Example 5] Quantitative qRT-PCR for Pyruvate Transporter Overexpression Transformant To investigate an expression level of a transcript (mRNA) of the PtPTP gene in the obtained transformants, RNA was isolated from both transformants, followed by performing qRT-PCR.

RNA isolation was carried out using an RNA purification kit, Hybrid-R (manufactured by GeneAll, Korea) according to the usage of the kit. The isolated RNA was converted into cDNA using the High-Capacity cDNA Reverse Transcription Kit (Applied Biosystems Inc.). The synthesized cDNA was subjected to reverse transcription-quantitative PCR (real-time PCR) using SYBR pre-mix Ex Taq (Takara Bio Inc) by means of a thermocycler, Thermal Cycler Dice Real Time System TP 810 (Takara Bio Inc). Here, a reaction condition was as follows: 30 seconds at 95° C.; 40 cycles of 5 seconds at 95° C. and 30 seconds at 58° C.; 15 seconds at 95° C.; 30 seconds at 60° C.; and 15 seconds at 95° C. Relative changes in gene expression levels were analyzed by the DDCT method (Pfaffl, 2001) using Thermal Cycler Dice Real Time System Software Ver. 5 (Takara Bio Inc). The TATA box-binding protein (TBP, JGI protein ID:10199) gene was used as an internal control as in the previous study (Seo et al. 2015).

Primers for qRT-PCR were as follows.

To investigate an expression level of PtPTP transcript, a forward primer (5'-TGGATGGCCTTGATCGGTTC-3'; SEQ ID NO: 10) and a reverse primer (5'-AACGCTCGCTTGGGACTAAA-3'; SEQ ID NO: 11) were used. In addition, as a primer set for synthesizing the TATA box protein (TBP) gene as an internal reference gene, a forward primer (5'-TTGCCAGTTACGAGCCAGAG-3'; SEQ ID NO: 12) and a reverse primer (5'-CGCCAGGTC-CATTTCCTTCT-3'; SEQ ID NO: 13) were used.

PtPTP transcript (mRNA) expression levels of the selected transformants are shown in FIG. 6.

As shown in FIG. 6, it was confirmed that the PtPTP transcript expression levels in the transformants, PTP-OE11 and PTP-OE16, increased 4.9 fold and 21.4 fold respectively, compared to a control (WT).

The confirmed transformants were deposited as patent resources at the Korean Collection for Type Cultures (KCTC), and given the following accession numbers.

KCTC13253BP: *Phaeodactylum tricornutum* CCMP632 PtPTP-OE11 KCTC13254BP: *Phaeodactylum tricornutum* CCMP632 PtPTP-OE16

[Example 6] Confirmation of Biomass and Lipid Increase in Pyruvate Transporter Overexpression Transformant To investigate whether a biomass production amount increased in the selected pyruvate transporter overexpression transformants, growth rate, biomass amount, and total lipid content thereof were measured as follows:

6.1. Cell Concentration (Growth Rate) Measurement

The cell concentration of microalgae was determined by counting cells using a hemocytometer (Neubauer). A result of a growth rate over time is shown in FIG. 7.

As shown in FIG. 7, the two transformants showed a normal growth rate with no difference, compared to the control algae (WT). Next, the transformants showing the normal growth curves were subjected to biomass and lipid content analysis.

6.2. Analysis of Total Biomass Amount and Total Lipid Amount

Biomass was filtered using a 1.2 µm Isopore membrane filter (RTTP; Merck Millipore, Cork, IRL) to harvest microalgae. The microalgae were dried in a 65° C. chamber for 24 hours, and then the weight thereof was measured.

Total lipid content was analyzed based on dry weight of biomass at each of 3, 5, 7 days after the first inoculation of microalgae, and a total lipid content was investigated on day 7, the stationary phase wherein growth was stopped and accumulation to a lipid component occurred.

In particular, wild-type microalgae (WT190.0), transformation microalgae PTP-OE11 and transformation microalgae PTP-OE16 were respectively incubated, and the incubated microalgae were centrifuged (2,000 g, 15 minutes), followed by removing a supernatant therefrom and harvesting a precipitate. 2 ml of chloroform, 2 ml of methanol, and 1 ml of 5% NaCl were added to the harvest, followed by vortexing for 2 minutes and then centrifugation (2,000 g, 10 minutes), thereby inducing layer separation. The bottom chloroform layer was carefully taken and collected in another tube. This process was repeated three times. The collected solution was contained in a pre-weighed aluminum dish, and the dish was slightly heated to evaporate chloroform. Next, after completely drying overnight in a 65° C. chamber, the dish was weighed to measure a lipid content. Growth curves of the transformants are shown in Table 1 and FIG. 8.

TABLE 1

|  |  | WT190.0 | PTP-OE11 | PTP-OE16 |
| --- | --- | --- | --- | --- |
| Biomass (mg/L) | Day 3 | 190.0 ± 12.2 (100%) | 211.0 ± 30.8 (111%) | 237.0 ± 38.6 (125%) |
|  | Day 5 | 269.3 ± 7.6 (100%) | 319.5 ± 23.4* (117%) | 337.8 ± 26.8* (125%) |
|  | Day 7 | 313.7 ± 21.1 (100%) | 353.7 ± 13.6 (113%) | 331.0 ± 15.7 (106%) |
| Lipid (mg/L) | Day 7 | 53.7 ± 3.5 (100%) | 62.6 ± 5.1* (117%) | 63.4 ± 3.9* (118%) |

As shown in FIG. 8, it was confirmed that biomass in the PTP overexpression transformants increased by 117% and 125%, respectively, at the exponential phase, Day 5, and total lipid contents therein increased by 117% and 118%, respectively, on Day 7 of incubation (* is a t-test result; confidence level of p-value <0.05). In conclusion, it was confirmed that the novel transformants in which the pyruvate transporter of the present invention was overexpressed exhibited increased biomass and lipid productivity.

The invention claimed is:

1. A vector, comprising a nucleic acid molecule encoding a pyruvate transporter comprising the amino acid sequence of SEQ ID NO: 1.

2. The vector according to claim 1, further comprising a promoter for overexpressing the nucleic acid molecule.

3. A transformant, comprising the vector according to claim 1.

4. *Phaeodactylum tricornutum* CCMP632 PtPTP-OE11 (KCTC 13253BP); or *Phaeodactylum tricornutum* CCMP632 PtPTP-OE16 (KCTC 13254BP) having improved biomass or lipid production capacity.

5. A method of producing biomass, the method comprising incubating the transformant according to claim 3, wherein the transformant is *Phaeodactylum tricornutum* CCMP632 PtPTP-OE11 (KCTC 13253BP) or *Phaeodactylum tricornutum* CCMP632 PtPTP-OE16 (KCTC 13254BP).

6. A composition comprising the vector according to claim 1 and/or a transformant comprising the vector.

7. A method of transforming a microorganism, the method comprising introducing a nucleic acid molecule encoding a pyruvate transporter comprising the sequence of SEQ ID NO: 1; and a promoter for overexpressing the nucleic acid molecule into a microorganism.

8. The method according to claim 7, wherein the nucleic acid molecule and the promoter are inserted into an expression vector.

9. A method of producing biodiesel, the method comprising incubating the transformant according to claim 3.

* * * * *

SEQUENCE LISTING

```
<160> NUMBER OF SEQ ID NOS: 13

<210> SEQ ID NO 1
<211> LENGTH: 396
<212> TYPE: PRT
<213> ORGANISM: Phaeodactylum tricornutum
```

<400> SEQUENCE: 1

```
Met Pro Met Ile Ala Pro Thr Ile Ser Thr Thr Thr Ser Thr Ala
1               5                   10                  15

Leu Ser Ala Thr Ser Leu Gln Ala Ala Asn Gly Glu Ala Ala Gly Lys
            20                  25                  30

Ser Phe Gly Gln Lys Leu Phe Glu Gly Tyr Glu Lys Thr Ala Asn Val
        35                  40                  45

Ala Thr Thr Leu Phe Pro Leu Trp Thr Val Leu Phe Thr Gly Leu Ala
    50                  55                  60

Leu Lys Ser Pro Ser Ser Phe Ala Trp Phe Thr Thr Glu Tyr Phe Thr
65                  70                  75                  80

Ala Gly Leu Ala Ala Leu Met Leu Ser Met Gly Ile Thr Leu Thr Pro
                85                  90                  95

Asn Asp Phe Lys Lys Val Ala Ala Arg Pro Asn Ala Thr Leu Met Gln
                100                 105                 110

Phe Ala Leu Cys Tyr Gly Met Met Pro Met Leu Ala Leu Gly Leu Gly
            115                 120                 125

Lys Ala Phe Ala Leu Glu Pro Ala Leu Ile Ala Gly Met Val Leu Val
130                 135                 140

Gly Ser Ile Asn Gly Gly Gln Ala Ser Asn Leu Cys Thr Tyr Ile Ala
145                 150                 155                 160

Arg Gly Asn Val Ala Leu Ser Val Leu Met Thr Thr Ala Thr Thr Leu
                165                 170                 175

Gly Ala Ile Val Met Thr Pro Leu Leu Cys Lys Ser Leu Leu Gly Ala
            180                 185                 190

Val Val Pro Val Asp Ala Ala Gly Ile Ala Lys Ser Thr Ile Gln Val
        195                 200                 205

Val Leu Ala Pro Ile Val Ile Gly Met Thr Thr Asn Lys Phe Phe Pro
    210                 215                 220

Arg Phe Val Glu Lys Ile Leu Pro Phe Ala Pro Val Val Gly Val Val
225                 230                 235                 240

Ser Thr Cys Leu Leu Val Ala Ser Ala Val Ala Gln Val Ala Glu Pro
                245                 250                 255

Ile Leu Asn Ala Gly Leu Arg Leu Gln Ile Pro Ile Met Leu Ile His
            260                 265                 270

Leu Leu Gly Gly Leu Val Gly Tyr Ile Leu Pro Arg Leu Thr Gly Phe
        275                 280                 285

Gly Glu Thr Ser Ser Arg Thr Met Ala Ile Glu Thr Ser Met Lys Ser
    290                 295                 300

Ser Ala Phe Gly Phe Leu Leu Ala Lys Leu His Phe Gly Asp Tyr Ala
305                 310                 315                 320

Ala Arg Val Pro Ser Ala Val Ser Val Val Trp Met Ala Leu Ile Gly
                325                 330                 335

Ser Leu Leu Ala Val Val Trp Arg Tyr Ile Pro Val Gly Thr Thr Gly
            340                 345                 350

Lys Phe Asp Arg Ser Leu Val Asp Lys Tyr Pro Pro Phe Ser Pro Lys
        355                 360                 365

Arg Ala Phe Gly Lys Phe Leu Gln Ser Val Gly Leu Gln Lys Lys Asp
    370                 375                 380

Asp Asp Ala Thr Pro Thr Pro Ser Val Thr Glu Ala
385                 390                 395
```

-continued

```
<210> SEQ ID NO 2
<211> LENGTH: 1211
<212> TYPE: DNA
<213> ORGANISM: Phaeodactylum tricornutum

<400> SEQUENCE: 2
atgccaatga ttgctcccac gatttctacg acgacgacgt ccactgctct ttccgcaacg      60
tctctccaag ccgctaacgg cgaggcagcc ggaaaatcct tcggtcagaa actctttgaa     120
ggctacgaaa agacggccaa cgtcgccacg acgctctttc ccctctggac cgtccttttc     180
accggtctcg ccctcaaaag cccgtcctcg ttcgcctggt ttaccaccga atactttacg     240
gcgggtctgg ccgcactcat gctctccatg gtatcacgc tcaccccaa cgatttcaaa      300 aaggtagccg cccgtcccaa cgccacgctc atgcagtttg ctctctgtta cggaatgatg     360
ccaatgctgg ctctgggact cggtaaggct ttcgccttgg aacccgcctt gattgccggt     420
atggtgttgg tcgggtccat caacggtgga caagcttcca acttgtgtac ctacattgcc     480
cggggtaacg tcgccttgtc ggtcctcatg accaccgcta ccaccttggg cgccatcgtc     540
atgaccccgc tcttgtgcaa gagcctcctg ggggccgtcg tacccgtcga cgctgctggg     600
atcgccaagt ccaccattca ggtcgtgcta gctccgattg tgattggtat gactaccaac     660
aaattcttcc cccggtttgt cgagaaaatc cttccgttcg ccccgttgt tggggtcgtc     720 tcgacctgtt tactggttgc cagtgcggtc gctcaagttg ccgaacccat cctgaacgcc     780
ggattgcgtt tacagatccc cattatgttg attcatcttt tgggaggact cgtcggctac     840
attttgcctc gtttgaccgg atttggcgag acgtcctccc gcaccatggc gattgaaacc     900
tccatgaaga gctccgcttt tggtttcctc ttggccaagc tgcactttgg cgactacgcg     960
gcccgtgtgc cttcggccgt ctccgtcgtg tggatggcct tgatcggttc cttgttggcc    1020
gtcgtatggc ggtacatccc ggtggaaacc accggcaagt tcgaccgttc cttggtggac    1080
aagtacccgc cctttagtcc caagcgagcg tttggaaaat tcctacagtc ggttggtctg    1140
caaaagaagg atgacgacgc gacaccgaca ccctcggtga cggaagcgta gtttctcgat    1200
gacggggata t                                                         1211

<210> SEQ ID NO 3
<211> LENGTH: 1468
<212> TYPE: DNA
<213> ORGANISM: Phaeodactylum tricornutum

<400> SEQUENCE: 3
atgccaatga ttgctcccac gatttctacg acgacgacgt ccactgctct ttccgcaacg      60
gtacgtacca atcgacaacg ataccgcaca catcgataca ataccaaccg agcgcgagag     120
aggattccgg tttcaccaca aagcagcgat cctcacggtc tttcttccta tatcctcttc     180
ttggtacagt ctctccaagc cgctaacggt gaggcagccg aaaatcctt cggtcagaaa      240 ctctttgaag gctacgaaaa gacggccaac gtcgccacga cgctcttccc cctctggacc     300
gtccttttca ccggtctcgc cctcaaaagc ccgtcctctt tcgcctggtt taccaccgaa     360
tactttacgg cgggtctggc cgcactcatg ctctccatgg catcacgct caccccccaac     420 gatttcaaaa aggtagccgc ccgtcccaac gccacgctca tgcagtttgc tctctgttac     480
ggaatgatgc caatgctggc tctgggactc ggtaaggctt tcgccttgga acccgccttg     540
attgccggta tggtgttggt cgggtccatc aacggtggac aagcttccaa cttgtgtacc     600
tacattgccc ggggtaacgt cgccttgtcg gtcctcatga ccaccgctac caccttgggc     660
```

```
gccatcgtca tgaccccgct cttgtgcaag agcctcctgg gggccgtcgt acccgtcgac    720
gccgctggga tcgccaaatc caccattcag gtacgttcat cgctgtccgc ctagtaacgc    780
gtagttgcag tacaccaccc actcgttgca ccgttcgtcg atggaggttc ctggagagca    840
gagctcacac attagtgttg ttgtcgctac gtttgcaggt cgtgctagct ccgattgtga    900
ttggtatgac caccaacaaa ttcttccccc ggtttgtcga gaaaatcctt ccgttcgccc    960
ccgttgttgg ggtcgtctcg acctgtttac tggttgccag tgcggtcgct caagttgccg   1020
aacccatcct gaacgccgga ttgcgtttac agatccccat aatgttgatt catcttttgg   1080
gaggactcgt cggctacatt ttgccccgtt tgaccggatt tggcgagacg tccgcccgca   1140
ccatggcgat tgaaacctcc atgaagagct ccgcctttgg tttcctcttg gccaagctgc   1200
actttggtga ctacgcggcc cgtgtgcctt cggccgtctc cgtcgtgtgg atggccttga   1260
tcggttcctt gttggccgtc gtatggcggt acatcccggt ggaaaccacc ggcaagttcg   1320
accgttcctt ggtggacaag tacccgcccc ttagtcccaa gcgagcgttt ggaaaattcc   1380
tacagtcggt tggtctgcaa aagaaggatg acgacgcgac accgacaccc tcggtgacgg   1440
aagcgtagtt tctcgatgac ggggatat                                      1468

<210> SEQ ID NO 4
<211> LENGTH: 29
<212> TYPE: DNA
<213> ORGANISM: Artificial
<220> FEATURE:
<223> OTHER INFORMATION: primer for Pyruvate transporter

<400> SEQUENCE: 4
atgccaatga ttgctcccac gatttctac                                       29

<210> SEQ ID NO 5
<211> LENGTH: 24
<212> TYPE: DNA
<213> ORGANISM: Artificial
<220> FEATURE:
<223> OTHER INFORMATION: primer for Pyruvate transporter

<400> SEQUENCE: 5
atatccccgt catcgagaaa ctac                                            24

<210> SEQ ID NO 6
<211> LENGTH: 27
<212> TYPE: DNA
<213> ORGANISM: Artificial
<220> FEATURE:
<223> OTHER INFORMATION: Xba I linker Forward primer

<400> SEQUENCE: 6
tctagatgcc aatgattgct cccacga                                         27

<210> SEQ ID NO 7
<211> LENGTH: 26
<212> TYPE: DNA
<213> ORGANISM: Artificial
<220> FEATURE:
<223> OTHER INFORMATION: Xba I linker Reverse primer

<400> SEQUENCE: 7
tctagacccc gtcatcgaga aactac                                          26

<210> SEQ ID NO 8
<211> LENGTH: 22
```

<212> TYPE: DNA
<213> ORGANISM: Artificial
<220> FEATURE:
<223> OTHER INFORMATION: EF2 promoter region primer

<400> SEQUENCE: 8
ctgtgaagcc gtggtgaatc tt                                              22

<210> SEQ ID NO 9
<211> LENGTH: 22
<212> TYPE: DNA
<213> ORGANISM: Artificial
<220> FEATURE:
<223> OTHER INFORMATION: PtPTP ORF region reverse primer

<400> SEQUENCE: 9
ccgggcaatg taggtacaca ag                                              22

<210> SEQ ID NO 10
<211> LENGTH: 20
<212> TYPE: DNA
<213> ORGANISM: Artificial
<220> FEATURE:
<223> OTHER INFORMATION: PtPTP forward primer

<400> SEQUENCE: 10
tggatggcct tgatcggttc                                                 20

<210> SEQ ID NO 11
<211> LENGTH: 20
<212> TYPE: DNA
<213> ORGANISM: Artificial
<220> FEATURE:
<223> OTHER INFORMATION: PtPTP reverse primer

<400> SEQUENCE: 11
aacgctcgct tgggactaaa                                                 20

<210> SEQ ID NO 12
<211> LENGTH: 20
<212> TYPE: DNA
<213> ORGANISM: Artificial
<220> FEATURE:
<223> OTHER INFORMATION: TATA box protein forward primer

<400> SEQUENCE: 12
ttgccagtta cgagccagag                                                 20

<210> SEQ ID NO 13
<211> LENGTH: 20
<212> TYPE: DNA
<213> ORGANISM: Artificial
<220> FEATURE:
<223> OTHER INFORMATION: TATA box protein reverse primer

<400> SEQUENCE: 13
cgccaggtcc atttccttct                                                 20